United States Patent [19]
Landry, Jr. et al.

[11] Patent Number: 5,090,962
[45] Date of Patent: Feb. 25, 1992

[54] NON-REUSABLE SYRINGE

[75] Inventors: Maurice J. Landry, Jr., Nashua, N.H.; Frederick L. Plouff, Wakefield, Mass.

[73] Assignee: FLP Enterprises, Inc., Andover, Mass.

[21] Appl. No.: 344,992

[22] Filed: Apr. 28, 1989

[51] Int. Cl.⁵ ............................................. A61M 5/00
[52] U.S. Cl. .................................. 604/110; 604/220; 604/228
[58] Field of Search ............... 604/110, 218, 220, 228; 128/917

[56] References Cited

U.S. PATENT DOCUMENTS

| | | | |
|---|---|---|---|
| 4,493,703 | 1/1985 | Butterfield | 604/110 |
| 4,731,068 | 3/1988 | Hesse | 604/110 |
| 4,775,364 | 10/1988 | Alles | 604/110 |
| 4,781,684 | 11/1988 | Trenner | 604/110 |
| 4,826,483 | 5/1989 | Molnar | 604/110 |
| 4,850,968 | 7/1989 | Romano | 604/110 |
| 4,863,427 | 9/1989 | Cocchi | 604/110 |
| 4,878,899 | 11/1989 | Plouff | 604/110 |
| 4,887,999 | 12/1989 | Alles | 604/110 |
| 4,915,700 | 4/1990 | Noonan | 604/195 |
| 4,958,622 | 9/1990 | Selenke | 128/765 |
| 4,973,309 | 11/1990 | Sulten | 604/110 |
| 4,978,339 | 12/1990 | Labouze et al. | 604/110 |
| 4,986,812 | 1/1991 | Perler | 604/110 |
| 4,995,869 | 2/1991 | McCarthy | 604/110 |
| 5,019,045 | 5/1991 | Lee | 604/110 |
| 5,021,047 | 6/1991 | Movern | 604/110 |
| 5,024,661 | 6/1991 | Wender et al. | 604/110 |

FOREIGN PATENT DOCUMENTS

WO8912476 12/1989 World Int. Prop. O. .......... 604/110

Primary Examiner—C. Fred Rosenbaum
Assistant Examiner—Mark O. Polutta
Attorney, Agent, or Firm—Pearson & Pearson

[57] ABSTRACT

A single use syringe in the form of a cylindrical barrel with a first end attached to a hypodermic needle. A plunger and piston in the barrel draw liquid into the syringe through the hypodermic needle and eject the liquid through the hypodermic needle. The plunger includes a detent formed at an intermediate location. An insert at the second end of the barrel includes at least one cantilevered, longitudinally extending resilient arm with a follower at a free end thereof that rides over the plunger. When the plunger is pushed to a final position, the follower drops into the plunger detent to block any further longitudinal motion of the plunger and piston preventing any subsequent use.

19 Claims, 4 Drawing Sheets

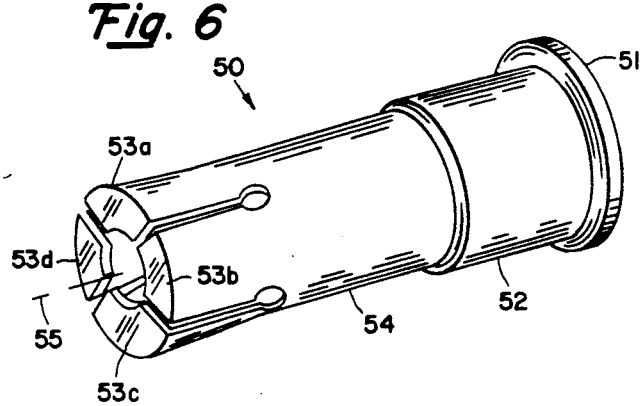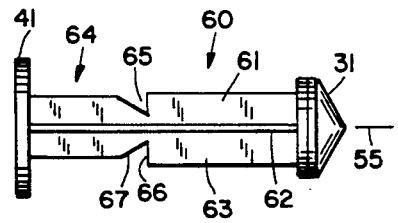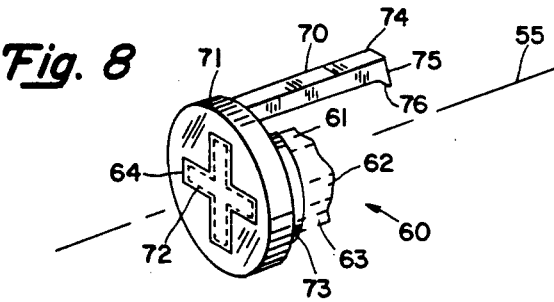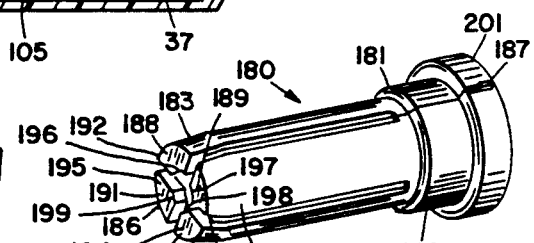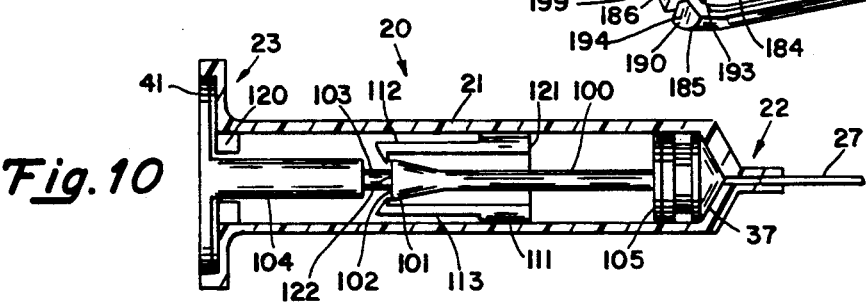

NON-REUSABLE SYRINGE

CROSS REFERENCE TO RELATED APPLICATION

Reference is made to U.S. Application Ser. No. 07/160,712 filed Feb. 26, 1988, now U.S. Pat. No. 4,878,899 by Frederick L. Plouff and titled "Disposable Syringe for One-Time Use".

BACKGROUND OF THE INVENTION

1. Field of the Invention

This invention is directed to syringes for medical use and more specifically to syringes that can be used only once.

2. Description of Related Art

Reference is made to the following Letters Patent of the U.S.:

| | | |
|---|---|---|
| 4,687,467 | (1987) | Cygielski |
| 4,699,614 | (1987) | Glazier |
| 4,713,056 | (1987) | Butterfield |
| 4,731,068 | (1988) | Hesse |

A syringe has several basic parts, namely: a barrel, a plunger and a piston. The barrel normally houses the piston and supports the plunger in the form of a push-rod, or the like, for moving the piston axially within the barrel. The plunger exits the barrel at one end thereof. The barrel supports a hypodermic needle or the like at the opposite end. In use, a person withdraws the plunger thereby moving the piston away from the needle and transferring medicine into a cavity formed between the needle end of the barrel and the piston. When the correct amount of medicine has been withdrawn, the needle is injected into a patient and the plunger is moved toward the needle end, forcing the medicine from the cavity through the needle into the patient.

In recent years, considerable effort has been expended to provide a syringe for medical use that is both disposable and not reusable. Some of these syringes include a push-rod and piston that are detachably interconnected by some mechanical coupling or operator. The operator couples the push-rod and piston during an initial withdrawal to transfer medicine from a storage container into the syringe. When the push-rod moves toward the needle end during an injection, however, the operator decouples the push-rod and piston. Any attempt to withdraw the push-rod thereafter separates the push-rod and the piston, so additional medicine cannot be transferred into the syringe. The Hesse and Glazier patents are examples of this approach.

In other syringes a mechanism affixed to the barrel captures the piston or the push-rod when all the medicine has been injected into a patient. This prevents any subsequent withdrawal of the push-rod so that no additional medicine can be transferred into the syringe. The co-pending Plouff patent application and the Butterfield patent are examples of this general approach.

Syringes fill because a partial vacuum is produced within the syringe as the push-rod and piston are withdrawn during a filling operation. In the Cygielski patent, a cutter near the needle end of the syringe punctures a seal formed by the piston as a dose of medicine is administered to a patient. If the push-rod and piston are subsequently withdrawn, air leaks through the punctured seal so no partial vacuum forms and no medicine can transfer into the syringe.

Each of these proposed constructions have certain disadvantages. For example, the Plouff patent application and the Butterfield and Cygielski patents incorporate elements within the liquid cavity so these elements contact the fluid directly. This complicates the sterilization process. Including elements within the cavity complicates sealing construction and can lead to leakage. Syringes such as suggested by the Glazier and Cygielski patents contain mechanisms for achieving the one use objective. However, these mechanisms are somewhat complex and can increase manufacturing costs.

SUMMARY OF THE INVENTION

Therefore it is an object of this invention to provide an improved syringe for medical use that can be used only once.

Another object of this invention is to provide a syringe for medical use that can be used only once and eliminates elements in the fluid cavity.

Yet another object of this invention is to provide a syringe for medical use that can be used only once in which the elements that prevent repeated use also limit the dose that can be drawn into the syringe.

In accordance with this invention, a syringe includes a cylindrical barrel means that supports a hypodermic needle at a first end thereof. Piston means define a fluid cavity between a first end of the barrel means and the piston means. A plunger moves the piston means axially from a first position adjacent the first end of the barrel, to a second position intermediate the first and other ends of the barrel means and to a third position intermediate said first and second positions but contiguous said first position. An insert disposed in the barrel means at the second end thereof includes a resilient clamp means that ride over the plunger during motion between the second and third position during filling and injection, but engage a detent means on the plunger means when the plunger moves to the first position, as when an injection has been completed. This locks the plunger in place and prevents further syringe use.

BRIEF DESCRIPTION OF THE DRAWINGS

This invention is pointed out with particularity in the appended claims. The various objects, advantages and novel features of this invention will be more fully apparent from a reading of the following detailed description taken in conjunction with the accompanying drawings in which like reference numerals refer to like parts, and in which:

FIG. 6 is a perspective view of the insert shown in FIGS. 1 through 5;

FIG. 7 depicts a plunger with a cruciform cross-section that can be used in the syringe of FIG. 1;

FIG. 8 depicts an insert that is useful with the plunger shown in FIG. 5;

FIG. 9 is a view of another embodiment of a syringe constructed in accordance with this invention with the plunger and piston positioned in a fully retracted position;

FIG. 11A is a perspective view of an embodiment of another insert.

FIG. 10 is another view of the syringe shown in FIG. 9 with the plunger being locked in place by the insert;

FIG. 11 is a detailed perspective view of the insert utilized in the syringes shown in FIGS. 9 and 10;

DESCRIPTION OF ILLUSTRATIVE EMBODIMENTS

Figure 1:
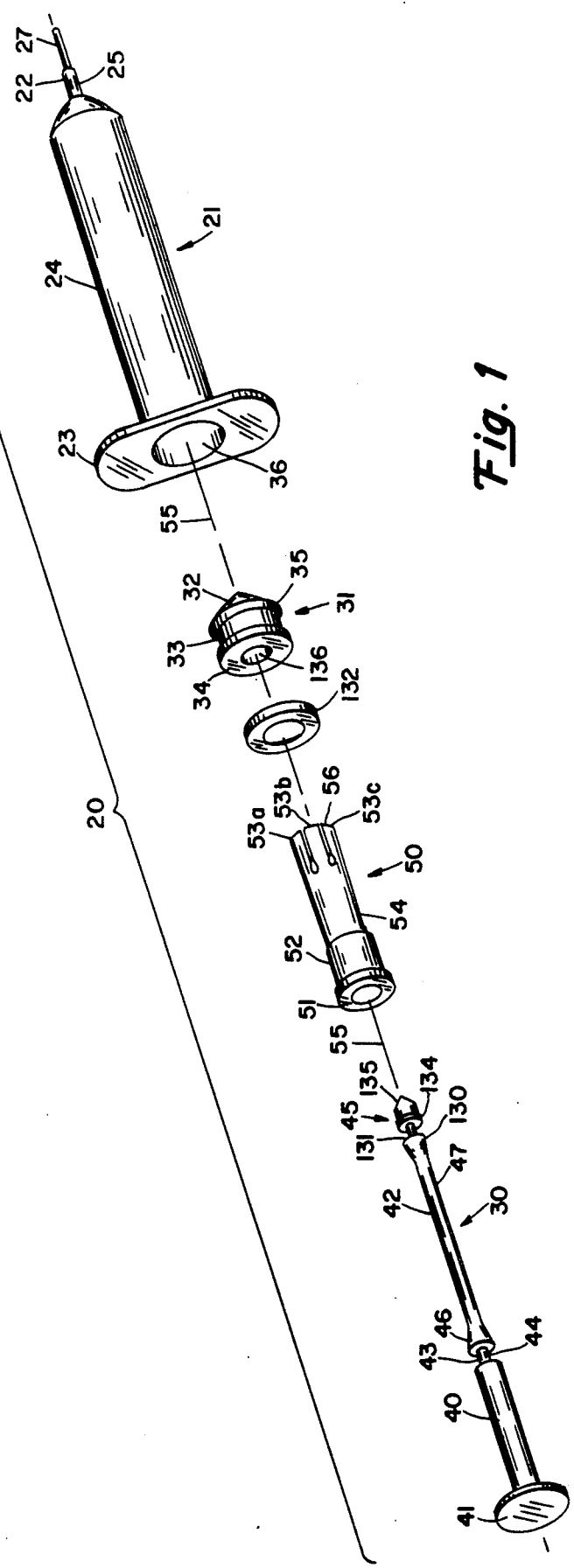
FIG. 1 is an exploded, perspective view of a barrel, plunger, piston and insert that are included in an embodiment of a syringe constructed in accordance with this invention.

Referring to FIGS. 1 through 5, a syringe 20 includes a cylindrical barrel 21 with a first end 22, a second end 23 and a body portion 24. The first end 22 has a concave, conical shape that reduces from the diameter of the body portion 24 to smaller diameter at a hypodermic needle attachment 25 with a passage 26 (shown in FIGS. 2-5). The attachment 25 receives a hypodermic needle 27 with internal passages for the subcutaneous administration of a liquid.

The syringe 20 also includes a plunger 30 that carries a piston 31 along the inner surface 36 within the barrel 21. The piston 31 has a convex conical end portion 32 that compliments the inner concave surface of the barrel 21 at the first end 22. A body portion 33 on the piston terminates longitudinally with two annular protuberances 34 and 35 that form a sliding seal with an internal surface 36 of the barrel 21.

Figure 2:
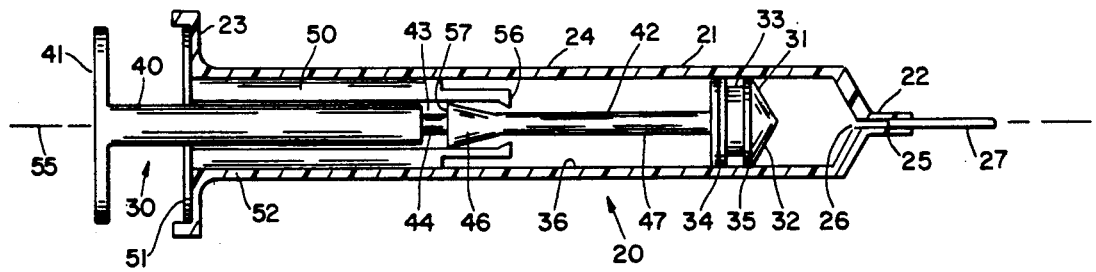
FIG. 2 depicts the syringe of FIG. 1 with the plunger positioned to begin filling of the syringe.
Figure 3:
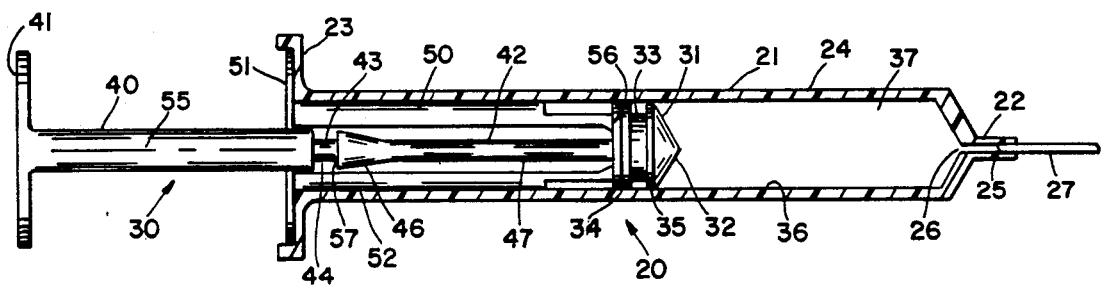
FIG. 3 is a view of the syringe in FIG. 2 in which the plunger is fully retracted.

As the plunger 30 moves from the position in FIG. 2 to the position in FIG. 3 during a filling operation with the hypodermic needle 27 in liquid, differential pressure forces the liquid through the needle 27 and passage 26 to fill a cavity 37. The cavity 37 increases in volume as the piston 31 moves toward the second end 23. When the plunger 30 then moves toward the first end 22, the piston 31 forces the liquid from the cavity 37 through the passage 26 and the needle 27. When the piston 31 reaches the first end 22, the convex portion 32 fits within the concave conical end portion 22 and thereby expels essentially all the liquid from the syringe 20.

In accordance with this invention, the syringe shown in FIGS. 1 through 5 is limited to one use by a locking mechanism that includes the plunger 30. In this specific embodiment the plunger 30 comprises a cylindrical push-rod 40 of a given diameter with an integral thumb pad 41 A cylindrical stem 42 is longitudinally aligned with and spaced from the push-rod 40 to form an intermediate detent area 43. A connecting stem 44 interconnects the push-rod 40 and the stem 42; the stem 44 may be formed integrally by molding or may comprise a central core member that is ultrasonically welded or otherwise affixed to the push-rod 40 and stem 42.

A free end 45 of the stem 42, shown in FIG. 1, engages the piston 31, as described in more detail later, with sufficient force to allow the stem 42 to withdraw the piston 31 and overcome the friction between the sealing protuberances 34 and 35 and the inner surface 36 of the barrel 21. The other end 46 of the stem 42 flares to a diameter of approximately the diameter of the push-rod 40. The diameter of an intermediate portion 47 of the stem 42 is slightly larger than or equal to the connecting stem 44 and less than the maximum diameter of the flared end portion 46.

The locking mechanism also includes a generally cylindrical insert 50 shown in detail in FIG. 6. The insert 50 comprises a cap 51, a body portion 52, and a series of longitudinally extending, circumferentially spaced arms 53a, 53b, 53c, 53d that cantilever from a reduced diameter support portion 54 of the body. Each arm 53 a, b, c, d can flex in a plane that is coplanar with each arm 53 a, b, c, d and a longitudinal axis 55 through the syringe 20. These arms 53 a, b, c, d act as followers that are biased toward the axis 55.

The syringe 20 is normally shipped as shown in FIG. 2 with the detent 43 area positioned inside a volume defined by the insert 50 as shown in FIG. 1. The thumb pad 41 and push-rod 40 then can be retracted to the position shown in FIG. 3 where the piston 31 abuts ends 56 of the insert 50. It will be apparent that the length of the insert 50 can be adjusted to control the volume of the cavity and thereby limit the quantity of liquid that can be withdrawn into the syringe. Moreover, in this position, the detent 43 still lies within and is covered by the barrel 21 and the insert 50. Thus, it is not possible to access the detent 43 to reduce the diameter of the flared end 46 in an attempt to defeat the locking mechanism.

Figure 4:
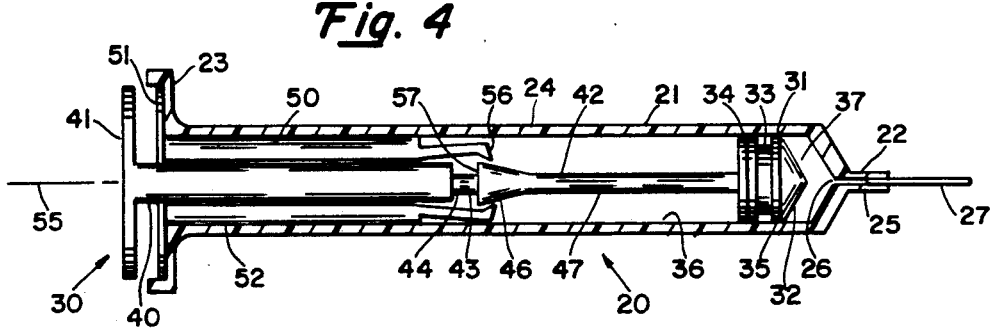
FIG. 4 is a view of the syringe as shown in FIG. 2 with the plunger positioned just prior to completion of an injection.
Figure 5:
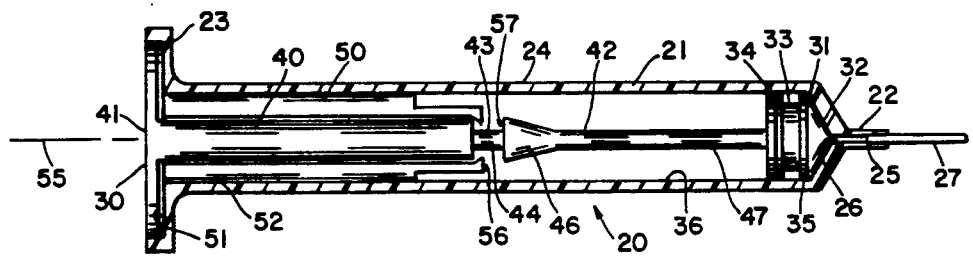
FIG. 5 is another view of the syringe in FIG. 2 wherein the insert clamps the plunger after use.
Figure 12:
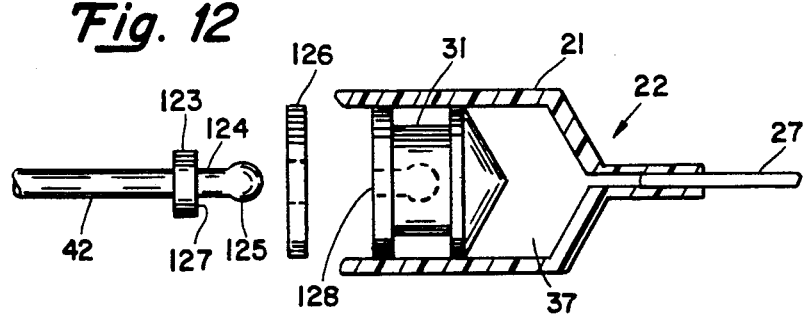
FIG. 12 is a detailed view to illustrate one connection that can couple the piston to a plunger.

As the thumb pad 41 moves toward the end 22, the piston 31 ejects the liquid in the cavity 37 from the syringe 20, and the arms 53 ride over the stem 42. The arms 53 follow the surface at the flared end 46 and move outward to flex the material adjacent the support portion 54 and increasing the bias on the arms 53 as shown in FIG. 4. As the injection is completed and the piston 31 moves to the position shown in FIG. 5, the portion flared end 46 passes to the right of the arms 53 whereupon the arms 53 snap, with an audible click, to a relaxed position within the detent area 43. A radial end surface 57 on the stem 42 will then strike the ends 56 of the arms 53 and block motion of the plunger 30 if there is an attempt to retract it. At the same time, the thumb pad 41 rests within a recess of second end 23 thereby to be flush with end 23 of the barrel. This makes it more difficult to retract the plunger 30 or even to grab it.

FIGS. 7 and 8 depict an alternative plunger structure for the locking mechanism that additionally prevents any rotation of the plunger. In some situations such rotation coupled with an attempt to retract the plunger might, with sufficient manipulation, expand the arms and release the detent mechanism. FIG. 7 depicts a unitary, non-rotatable plunger 60 with a thumb pad 41 that supports a piston 31. This plunger 60 has four radial fins 61, 62, 63 and 64 extending from a central portion along the length of the plunger 60 so the plunger 60 has cruciform cross-section. V-notches 65 at the same longitudinal position in each of fins 61 through 64 have edges 66 in a radial plane that intersect oblique edges 67.

Referring to FIG. 8, an insert 70 for the plunger 60 (shown partially in phantom) comprises a cap portion 71 with a cruciform aperture 72 therein that conforms to the cross section of the fins 61 through 64. The cap 71 may also have a reduced shoulder 73 that fits within the syringe barrel for supporting arms 74 with end surfaces 75 and inwardly extending followers 76. Prior to a filling operation, the notches 65 in the plunger 60 shown in FIG. 7 are positioned within the volume defined by the insert 70. The arms 74 are stressed as they are parallel to the axis 55 and have been flexed outward from a normally relaxed orientation. The plunger can then be retracted until the piston 31 in FIG. 5 abuts the end surfaces 75. As the plunger moves toward the first end 22 of the barrel 21 shown in FIG. 1, liquid is ejected through the needle 27 and the followers 76 ride along the edges of the fins 61 through 64 toward the notches 65. As the injection is completed, the followers 76 overlie the notches 65, so the arms 74 relax and the followers 76 snap into the notches 65. Any further withdrawal of the plunger 60 is blocked by interference between the end surfaces 75 and the radial notch surface edges 66. Moreover, the cruciform aperture 72 and fins 61 through 64 prevent any plunger rotation relative to the insert 70 thereby to thwart any attempts to override the locking mechanisms.

FIGS. 9 and 10 illustrate an alternative for locking the plunger after a first injection. In this particular application, a stem 100, that replaces the stem 42 shown in FIG. 1, has a flared portion 101 and end surface 102 that forms a detent area 103 with a cylindrical push-rod 104, or a non-rotatable rod as shown in FIGS. 7 and 8. At the opposite end of the stem 100, a portion 105 that captures the piston 31.

Still referring to FIGS. 9 and 10 and FIG. 11 an insert 110 has a cylindrical body 111 that fits closely to the internal surface 36 of the barrel 21. Two arms 112 and 113 extend from the body 111 toward the second end 23 of the syringe 20. In this embodiment the arms 112 and 113 have an arcuate cross section and encompass essentially a semicircle. Each of the arms 112 and 113 and terminates in an internal follower 114 with an oblique cam surface 115 and a radial end surface 116.

FIG. 11A shows another insert 180 having a pair of cylindrical bodies 181 and 182 that fit closely to the inside of the barrel. Each cylindrical body has a cap 201 and may be connected by a clam like hinge 187. A plurality of elongated arms 183, 184 185 and 186 extend from the body toward the first end 22 of the syringe 20. In this embodiment the arms 183, 184, 185 and 186 have an arcuate cross section and encompass essentially a semicircle. The plurality of arms terminate in a plurality of internal followers 188, 189, 190, 191 with oblique cam surfaces 192, 193, 194 and 195 and a plurality of radial end surfaces 196, 197, 198, and 199.

As shown the plunger can be withdrawn from a shipping position by withdrawing the thumb pad 41 from the syringe. An end insert 120 with an aperture therethrough guides and supports the push-rod 104. Retraction continues until the piston 31 abuts an end surface 121 of the insert 110.

During injection, the plunger moves the piston 31 toward the end 22 and the needle 27. As the piston 31 reaches the end 22, the flared end portion 101 separates the arms 112 and 113 as the followers 114 ride along the stem 100. This deflection stresses the arms 112 and 113, so they snap into a locking position when the stem 101 passes the followers 114 and they snap into the detent area 103. Further use is blocked by interference between the radial end surfaces 116 on the arms 112 and 113 and a radial end surface 112 on the stem 100.

There are several structures for connecting a plunger and piston shown in each of the foregoing FIGS. 12 through 16. For example, a piston 31 and a stem 42 of the type shown in FIG. 1 could attach through a ball-and-socket joint shown in FIG. 12. More specifically, the stem 42 terminates in a flange 123 with a short axially extending shank 124 that terminates in a ball 125. A washer 126 slides over the ball 125 and rests against a radial end surface 127 on the flange 123. A ball socket 128 is formed in the piston 31 to capture the ball 125 on the end of the stem 42. The specific dimensions of the ball 125 and ball socket 128 are not critical, so long as the ball 125 and socket 128 do not separate when the stem 42 or 100 is retracted.

When the piston 31 is driven toward the end 22 of the syringe such as shown in FIG. 1, the stem 42, particularly the ball 125, could produce excessive point forces on the piston 31 thereby deflecting and deforming it with a possible failure of the seal between the piston 31 and the internal surface 36 of barrel 21. The washer 26, whether merely placed over the ball or formed integrally therewith, distributes forces evenly over the end of the piston 31. Further, the interference between the washer 126 and the arms 53 in FIGS. 2 through 5, for example, provides a positive stop and limit on dose.

Figure 13:
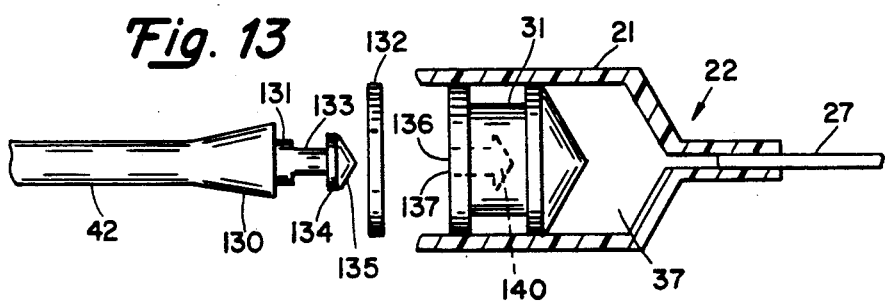
FIG. 13 is a detailed view of another connection.

FIGS. 1 and 13 depict the stem 42 with a flared strengthening portion 130 that terminates in an axially extending shoulder 131 for supporting a flat washer 132. An axially extending reduced diameter shank 133 terminates in an end fitting with a cylindrical shoulder 134 and a conical end section 135. The piston 31 has a conforming section 136 formed therein with a cylindrical passage 137 terminating in an enlarged cavity 140. When the washer 132 slides onto the shoulder 131 and the piston 31 is pushed over the end portion 134 and shank 133, the stem 42 firmly grips the piston 31.

Figure 14:
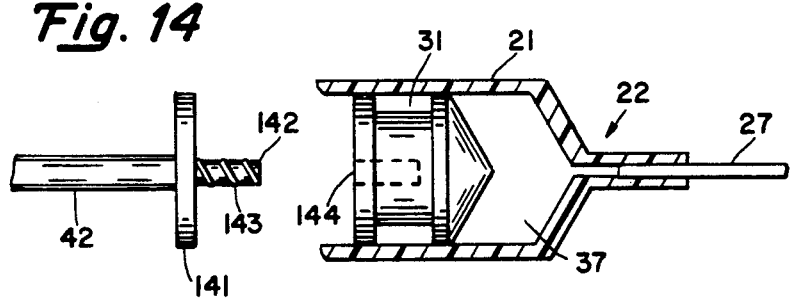
FIG. 14 is a detailed view of another piston-to-plunger connection.

FIG. 14 depicts another connection between a stem 42 and a piston 31. In this embodiment, the stem 42 has an integral flange 141, rather than a separate washer, and an extension 142 with a helical thread 143. A passage 144 is formed in the piston 31 and is undersized with respect to the diameter of the extension 142. When the piston 31 is forced over the extension 142, the material relaxes about the helical thread 143 to lock the piston 31 to the stem 42.

Figure 15:
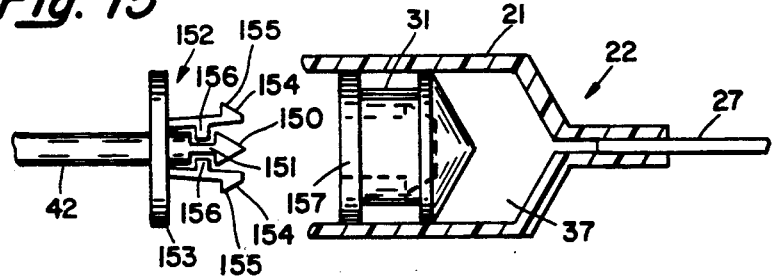
FIG. 15 is a detailed view of another piston-to-plunger connection.

Now referring to FIG. 15, the stem 42 is modified to include a conical end section 150 and an interconnecting shank 151 of reduced diameter. In this embodiment, a washer assembly 152 comprises a base flange 153 and two or more axially extending arms 154. Each arm 154 terminates in a projection 155 that extends radially outward and includes followers 156 that are intermediate the length of the arms and extend radially inward.

In assembly, the washer assembly 152 is forced into a cavity 157 in the piston, the arms 154 being compressed during insertion. Thereafter, the stem 42 is inserted forcing the arms 154 apart as the conical end section 150 passes the followers 156. When the stem 42 is fully inserted, the followers 156 snap against the shank 151 and locking the washer assembly 152 to the stem 42. In addition, the followers 156 continue to expand the arms 154 into a locking relationship with the piston 31.

Figure 16:
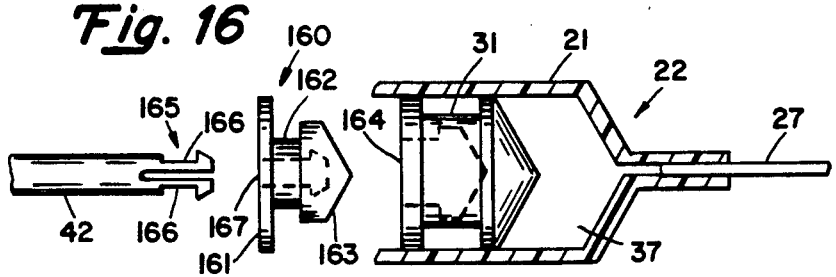
FIG. 16 is a detailed view of yet another piston-to-plunger connection.

A similar connection is shown in FIG. 16. A washer assembly 160 has an annular base 161 of a given diameter, and intermediate body portion 162 of a smaller diameter and an end section 163 of intermediate diameter. This assembly 160 is inserted into a corresponding cavity 164 of the piston 31 to lock the piston 31 and the washer assembly 160 together. The stem 42 terminates in a bifurcated section 165 with locking arms 166.

These are assembly inserted into a complementary cavity 167 in the washer these are assembly 160 thereby locking the washer assembly 160 and the piston 31 to the stem 42.

In summary, there have been described a number of embodiments of a syringe that is limited to a single use. In each embodiment, the syringe includes a barrel, a plunger with a detent portion and an insert with flexible arms positioned coaxially in the barrel to coact with the detent and block plunger motion after an injection. In accordance with certain objectives of this invention, all the elements are positioned outside the liquid cavity so there is no contact with the liquid. Moreover, the detent and arms are located inside the syringe, so there is no access to the locking mechanism even when the plunger is fully retracted.

It will be apparent that a number of variations of the basic concepts disclosed in the several syringe embodiments can be implemented. The syringe will include diverse end configurations to accommodate different hypodermic needles. The second end 23 may terminate as shown or with finger grip extensions. A given syringe may use a plunger with a cylindrical, a cruciform or other cross-sections. Two classes of coupling between the plunger and piston have been disclosed; other couplings are also possible. Generally these syringes will be constructed from moldable materials and by processes that are well known in the art. However, this invention is not limited to such materials and processes. Therefore, it is the object of the appended claims to cover all such variations and modifications as come within the true spirit and scope of this invention.

What is claimed as new and desired to be secured by Letters Patent of the U.S. is:

1. A syringe for a single administration of a fluid through a hypodermic needle comprising:
    A. cylindrical barrel means having a smooth internal surface and passage means at a first end for supporting the hypodermic needle and transferring fluid between the hypodermic needle and a liquid cavity formed in said barrel means,
    B. piston means in said barrel means including slidable sealing means for engaging said smooth internal barrel surface thereby to define said liquid cavity between said first barrel end and said piston means,
    C. plunger means connected to said piston means for moving said piston means along a longitudinal axis to a first position contiguous said first end of said barrel means, to a second position intermediate said barrel means and to a third position intermediate said first and second positions closely adjacent said first position, said plunger means having detent means formed therewith, positioned at a location remote from said piston means, and
    D. insert means internally of a barrel means and intermediate the length thereof for limiting the motion of said plunger means and said piston means, said insert means having a body portion for engaging the internal surface of said barrel means, a plurality of longitudinally extending circumferentially spaced arms pivoted from said body means, biased toward the longitudinal axis and extending toward the end opposite said first end of said cylindrical barrel means and follower means at the end of each of said arms for riding on said plunger means and engaging said detent means when said plunger moves to said first position.

2. A single use syringe as recited in claim 1 wherein said plunger means has a first connecting means formed thereon and said piston has a second connecting means formed thereon, said first and second connection means being detachably interconnected.

3. A single use syringe as recited in claim 1 wherein said first end of said barrel means has a predetermined interior cross section and piston means comprises:
    i. a cylindrical body portion,
    ii. an end portion that corresponds in cross section to the predetermined cross section of the first end of said barrel means, and
    iii. plural spaced circumferentially and radially extending sealing surfaces for engaging said barrel means thereby to define a sealed cavity between said piston means and said first end of said barrel means.

4. A single use syringe as recited in claim 3 additionally comprising planar means disposed on said plunger means abutting said piston means, said planar means transferring any compressive force from said plunger means to said piston means during an injection.

5. A single use syringe as recited in claim 4 wherein said plunger means has a first connecting means formed thereon and said piston has a second connecting means formed thereon, said first and second connection means being detachably interconnected.

6. A single use syringe as recited in claim 4 wherein said plunger means and said piston means are interconnected by:
    i. first connection means at an end of said plunger means,
    ii. second connection means formed in said piston means, and
    iii. intermediate connecting means coupling said first and second connection means.

7. A single use syringe as recited in claim 1 wherein a radial surface on said body means of said insert means facing said first end engages said piston means thereby to define the second longitudinal position of said plunger means and the maximum volume of said syringe cavity.

8. A single use syringe as recited in claim 7 wherein said plunger means comprises:
    i. push-rod means for operating said syringe,
    ii. first stem means longitudinally spaced from said push-rod means having a first end for connection to said piston means, and
    iii. second stem means between said push-rod means and the second end of said first stem means, said second end of said first stem means and said push-rod means constituting said detent means.

9. A single use syringe as recited in claim 8 wherein said insert means comprises four equiangularly spaced arms with follower portions at the free ends thereof for engaging said push-rod means.

10. A single use syringe as recited in claim 1 wherein said plunger means comprises:
    i. push-rod means for operating said syringe,
    ii. first stem means longitudinally spaced from said push-rod means having a first end for connection to said piston means, and
    iii. second stem means between said push-rod means and the second end of said first stem means, said second end of said first stem means and said push-rod means constituting said detent means.

11. A single use syringe as recited in claim 10 wherein said insert means comprises four equiangularly spaced arm means with follower portions at the free ends thereof for engaging said push-rod means.

12. A single use syringe as recited in claim 1 wherein said plunger means and said piston means are interconnected by
1. first connection means at a end of said plunger means,
2. second connection means formed in said piston means, and
3. intermediate connecting means coupling said first and second connection means.

13. A syringe for a single administration of a fluid through a hypodermic needle comprising:
   A. cylindrical barrel means having a smooth internal surface and passage means at a first end for supporting the hypodermic needle and transferring fluid between the hypodermic needle and a liquid cavity formed in said barrel means,
   B. piston means in said barrel means including slidable sealing means for engaging said smooth internal barrel surface thereby to define said liquid cavity between said first barrel end and said piston means,
   C. plunger means connected to said piston means for moving said piston means along a longitudinal axis to a first position contiguous said first end of said barrel means, to a second position intermediate said barrel means and to a third position intermediate said first and second positions closely adjacent said first position, and said plunger means having a cruciform cross section comprising a plurality of longitudinally extending radial fins and notch means formed at an intermediate location in at least one of said fins to engage a resilient arm means, and
   D. insert means internally of said barrel means and spaced toward a second end of said barrel means from said first end, said insert means having at least one resilient arm means for riding over one of said longitudinally extending radial fins of said plunger means during motion between said second and third plunger positions and for engaging said notched means when said plunger means moves to said first position.

14. A single use syring as recited in claim 13 wherein said plunger means has a first connecting means formed thereon and said piston has a second connecting means formed thereon, said first and second connection means being detachably interconnected.

15. A single use syringe as recited in claim 13 wherein said plunger means and said piston means are interconnected by:
   1. first connection means at an end of said plunger means,
   ii. second connection means formed in said piston means, and
   iii. intermediate connecting means couping said first and second connection means.

16. A single use syringe as recited in claim 13 wherein said plunger means has a cruciform cross section and said insert means includes cap means with a cruciform aperture therethrough for allowing longitudinal motion of, but blocking rotation of, said plunger means relative to said insert means.

17. A single use syringe as recited in claim 16 wherein said insert has four equiangularly spaced arms with follower portions at the free end thereof for engaging said notch means on each of longitudinally extending radial fins.

18. A single use syringe as recited in claim 16 wherein said plunger means has a cruciform cross section and said insert means includes cap means with a cruciform aperture therethrough for allowing longitudinal motion of, but blocking rotation of, said plunger means relative to said insert means.

19. A single use syringe as recited in claim 18 wherein said insert has four equiangularly spaced arms with follower portions at the free ends thereof for engaging said notch means on each of said longitudinally extending radial fins.

* * * * *